(12) United States Patent
Liu et al.

(10) Patent No.: US 8,691,568 B2
(45) Date of Patent: Apr. 8, 2014

(54) METHOD FOR PREPARING CELL POPULATIONS WITH ANTI-TUMOR IMMUNE RESPONSE ACTIVITY

(76) Inventors: Hua Liu, Shanghai (CN); Wei Yang, Shanghai (CN)

( * ) Notice: Subject to any disclaimer, the term of this patent is extended or adjusted under 35 U.S.C. 154(b) by 903 days.

(21) Appl. No.: 12/515,871

(22) PCT Filed: Nov. 22, 2006

(86) PCT No.: PCT/CN2006/003136
§ 371 (c)(1), (2), (4) Date: Dec. 18, 2009

(87) PCT Pub. No.: WO2008/061392
PCT Pub. Date: May 29, 2008

(65) Prior Publication Data
US 2010/0215628 A1 Aug. 26, 2010

(51) Int. Cl.
*C12M 1/00* (2006.01)
*C12N 5/00* (2006.01)
*C12N 5/02* (2006.01)
*C12N 5/07* (2010.01)

(52) U.S. Cl.
USPC ......... 435/347; 435/283.1; 435/325; 435/810

(58) Field of Classification Search
None
See application file for complete search history.

(56) References Cited

U.S. PATENT DOCUMENTS

| | | | | |
|---|---|---|---|---|
| 4,721,096 A | * | 1/1988 | Naughton et al. | 128/898 |
| 5,032,508 A | * | 7/1991 | Naughton et al. | 435/32 |
| 6,054,489 A | * | 4/2000 | Lorens et al. | 514/654 |
| 6,432,653 B1 | * | 8/2002 | Okarma | 435/7.21 |
| 6,548,299 B1 | * | 4/2003 | Pykett et al. | 435/377 |
| 2006/0165667 A1 | * | 7/2006 | Laughlin et al. | 424/93.21 |

FOREIGN PATENT DOCUMENTS

| | | |
|---|---|---|
| CN | 101007999 A | 8/2007 |
| WO | WO 96/29394 A1 | 9/1996 |
| WO | WO 98/16738 A2 | 4/1998 |
| WO | WO 2007/107038 A1 | 9/2007 |

* cited by examiner

*Primary Examiner* — Debbie K Ware
(74) *Attorney, Agent, or Firm* — Ming Chow; Sinorica, LLC

(57) ABSTRACT

The invention provides a method for preparing cell populations with anti-tumor immune response activity, which includes co-culturing tumor and mononuclear cell in a three-dimensional cell culture device, separating and amplifying the cell populations with anti-tumor immune response activity from the cultures. The present invention, at the same time, discloses the cell populations with anti-tumor immune response activity obtained by the method and the kit comprising the cell populations.

9 Claims, 4 Drawing Sheets

METHOD FOR PREPARING CELL POPULATIONS WITH ANTI-TUMOR IMMUNE RESPONSE ACTIVITY

Figure 1:
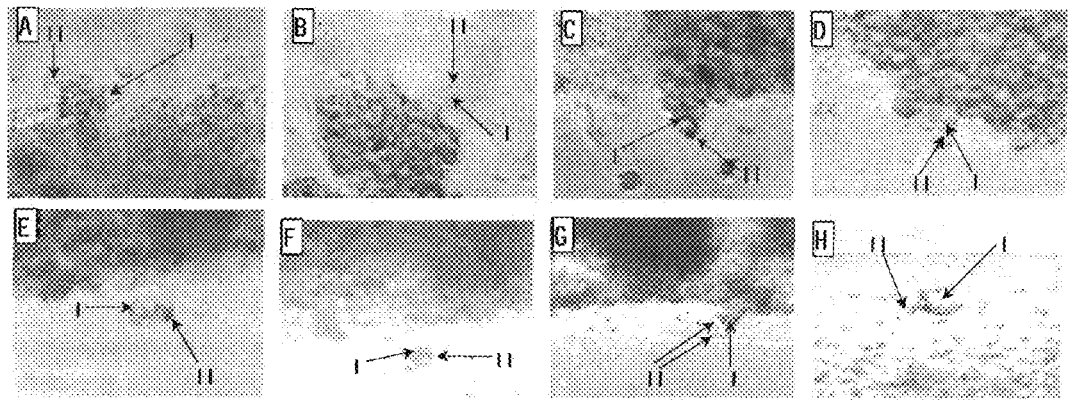

The present application is a U.S. national stage filing under 35 USC 371 of PCT/CN06/03136 filed Nov. 22, 2006.

TECHNICAL FIELD

The present invention belongs to the fields of biotechnology and immunology, and involves a method for preparing a group of cell populations with an anti-tumor immune response activity, and the sensitized cell populations with anti-tumor immune response activity prepared by said method.

BACKGROUND ART

Malignant tumors have become one of the main diseases that threaten human health and survival. The conventional therapies of tumor such as surgical operation, radiation therapy and chemotherapy involve external forces, which include exscinding tumors directly, killing tumor cells with radiation, or by chemotherapeutics. Chemotherapy and radiation therapy usually are unable to resolve the issues like tumor metastasis and recurrence. Moreover, these treatments always have severe toxic effects and damage the normal cells. In particular, radiation therapy and chemotherapy will damage the immune system, especially cell-mediated immunity which plays an important role in the body's anti-tumor defense. Increasing attention has been paid to biological treatments which are based on immunotherapy and promoted by the developments of modern oncology, molecular biology, theoretical immunology, biotechnology, and genetic engineering technology. Biological therapy, originally used to fight against cancers, also plays an important role in the prevention and treatment of infections, immunodeficiency, autoimmune diseases, etc., even in transplant rejection and anti-aging.

Cancer biotherapy, by means of various bioactive agents and methods, can stimulate, activate and regulate the body's immune and anti-cancer functions so the body can inhibit or even eliminate the growth of tumor cells, which shows great potential in therapeutics.

The investigation and development of a therapeutic cancer vaccine is a great challenge. Presently, satisfactory therapeutic cancer vaccines which can treat tumors or tumor cells effectively have still not been obtained, and thus patients' survival time cannot be prolonged significantly and tumors cannot be killed reliably.

In order to establish an effective vaccine for active specific immunotherapy, several obstacles must be overcome. Firstly, due to the poor specificities of tumor antigens or large tumor burdens, and patients' overall immunodeficiency caused by pre-chemotherapy as well as other factors, it is very difficult to induce the immune response of active specific immunotherapy which aims at tumor antigens. Secondly, because the antigenicity of tumor cells (particularly the immunogenicity of human spontaneously occurred tumors) is generally very weak, it may be not easy for the vaccine immunization to induce an adequate immune response to shrink the tumor. Thirdly, because of the heterogeneity in the expression of the tumor antigen, most patients need to be immunized by various antigens simultaneously. Fourthly, one of the main problems of developing a cancer vaccine is that it is hard to build an ideal animal model which is similar to the patients' clinical situation.

Although passive specific immunotherapy, namely transferring sensitized tumor-specific T lymphocytes, can treat the tumor of experimental animals effectively (confirmed in the late 60s and the early 70s), many issues including insufficient sensitized T lymphocytes, the difficulty of rejection reaction to be induced due to the weakness of antigens of the spontaneous tumors, and the incompatibility of sensitized T lymphocytes obtained from animal experiments for humans, hinder the study and the treatment of sensitized T lymphocytes. The biggest problem for the application of adoptive cellular immune therapy is how to obtain sufficient sensitized tumor-specific T lymphocytes.

Active non-specific immunity can stimulate the immune system by non-specific stimulation to enhance non-specific immune reactions; it can improve the immune reactions to existing tumors. The majority of active non-specific immunotherapy applied on humans in the past is not successful and most of them have not been used today. Almost all of the active non-specific treatments for patients who had advanced cancers are unsuccessful.

Passive non-specific immunotherapy, such as LAK/IL-2 and TIL/TDAK (tumor-derived activated killing cells) therapies, mainly aims at killing tumor cells by means of infusing their autologous or allogenic non-specific effectors. However, the effectiveness of these therapies are limited and need to be improved. For example, patients' insufficient autologous LAK precursor cells, along with slow amplification and limited efficacy, all lead to the ineffectiveness of the treatment. Moreover, patients usually cannot tolerate it due to serious side effects brought upon by repeated applications of high-dose rIL-2. The biggest disadvantages of TDAK therapy (which are more obvious than that of LAK therapy) are that it is time-consuming, laborious, and costly. The activity of TIL depends on the type, size and the extent of necrosis of the tumor, and not all tumors are infiltrated by lymphocytes. As a matter of fact, in most tumors it is difficult to obtain autologous tumor-specific TIL. The proliferative capability and anti-tumor activity of TIL will be reduced along with prolonged couture time. In addition, apoptosis can be found in some of the cells in the course of the cell culture. The TIL obtained from the tumors that produce immunosuppressive factors may be unable to proliferate, similar to the TIL obtained from metastatic tumors. In view of this, how to achieve these high tumor-reactive lymphocyte subsets and amplify them in vitro becomes the important issue of TIL/TDAK.

Therefore, it is urgent to develop a new concept and adopt a new approach to prepare cancer vaccines and to overcome the various problems associated with current immune therapies mentioned above.

SUMMARY OF THE INVENTION

The present invention aims at providing a method to prepare cell populations with anti-tumor immune response activity and the sensitized cell populations with anti-tumor immune response activity prepared by said method.

In the first aspect of the present invention, it provides a method to prepare cell populations with anti-tumor immune response activity and the method includes:

(1) co-culturing the tumor and mononuclear cells in a three-dimensional cell culture device, thereby obtaining the cultures which comprises cell populations with anti-tumor immune response activity;

(2) separating the cell populations with anti-tumor immune response activity from the cultures obtained from step (1).

wherein, the three-dimensional cell culture device includes:

(a) a container with liquid cell culture medium; and (b) a three-dimensional cell culture unit in the liquid cell culture medium, the three-dimensional cell culture unit includes empty cavities used for cell culture and empty cavity walls used to define the empty cavities; the empty cavity walls contain biodegradable materials to which cells can adhere and grow; in addition, nutritional ingredients and the products of cell metabolism can permeate the empty cavity walls;

the tumor and mononuclear cells are put together into the empty cavities of three-dimensional cell culture unit while they are being cultured.

In another preferable embodiment of the present invention, the tumor is selected from tumor cells, inactivated tumor cells, the cleavage products of tumor cells, proteins, polypeptides or other antigens obtained from tumor cells.

In another preferable embodiment of the present invention, the tumor is autologous or allogenic tumor.

In yet another preferable embodiment of the present invention, the mononuclear cells are autologous or allogenic cells.

In another preferable embodiment of the present invention, the number of the cell populations with anti-tumor immune response activity obtained from step (2) is $1\times10^5$-$1\times10^{11}$; more preferably, it is $1\times10^6$-$1\times10^{10}$; and most preferably, it is $1\times10^7$-$1\times10^9$.

In another preferable embodiment of the present invention, the mononuclear cells include monocytes, lymphocytes and basophilic cells.

In another preferable embodiment of the invention, the cell populations with anti-tumor immune response activity can be made into a pharmaceutical composition.

In another preferable embodiment of the present invention, the pharmaceutical composition is a vaccine.

In another preferable embodiment of the present invention, the tumor cells are obtained from the tumor tissues, malignant ascites, pleural effusion, or tumor cell lines of cancer patients.

In yet another preferable embodiment of the present invention, the cell populations with anti-tumor immune response activity include: tumor-infiltrating lymphocytes (TIL), lymphokine-activated killer cells (LAK), natural killer cells (NK), tumor-associated macrophages (TAM), activated killer monocytes (AKM), cytotoxic T lymphocytes (CTL) and/or dendritic cells (DC).

In another preferable embodiment of the present invention, the proportion of mononuclear cells and tumor cells involved in the step (2) is (5-100):1; more preferably, it is (5-50):1 and most preferably, it is (10-25):1.

In another preferable embodiment of the present invention, the co-culture time of the tumor cells and the mononuclear cells involved in the step (2) is 3-60 days; more preferably, it is 7-28 and most preferably, it is 14-21 days.

In another preferable embodiment of the present invention, the materials which can promote the growth of mononuclear cells can be added into the culture medium involved in the step (2).

In another preferable embodiment of the present invention, the substances which can promote the growth of mononuclear cells are cytokines. More preferably, it is IL-2 and the concentration is 90-10000 IU in general.

In yet another preferable embodiment of the present invention, antigen-presenting cells (APC) can also be added into the culture medium involved in the step (2).

In another preferable embodiment of the present invention, the proportion of APC and mononuclear cells is 5:100, and more preferably, it is 1:100.

In another preferable embodiment of the present invention, the antigen-presenting cells are dendritic cells (DC).

In another preferable embodiment of the present invention, the method also includes: amplifying the sensitized cell populations with anti-tumor immune response activity separated from the step (2) in vitro and putting it into a container so as to form a kit.

In the second aspect, the invention provides a kind of cell population with anti-tumor immune response activity obtained by the method.

In the third aspect, the invention provides a kit which includes:

a container, and the cell populations with anti-tumor immune response activity contained in the container, which is obtained by the abovementioned method.

In another preferable embodiment of the present invention, the number of the cell populations with anti-tumor immune response activity is $1\times10^5$-$1\times10^{11}$.

In another preferable embodiment of the present invention, the cell populations with anti-tumor immune response activity are put into the conventional infusion liquid; and in the more preferable embodiment, the conventional infusion liquid is 40 ml of 25% normal human serum albumin and 160 ml of normal saline which are put into the container.

In the fourth aspect, the invention provides the use of the cell populations with anti-tumor immune response activity obtained by said methodsin the preparation of anti-tumor drugs.

In the fifth aspect, the invention provides a method for the treatment of tumor, it includes:

infusing the cell populations with anti-tumor immune response activity obtained by the method into the patient's body.

In another preferable embodiment of the present invention, the routes of administration include intravenous, pleural, abdominal cavity, intraspinal, intradermal and subcutaneous injections, injecting into tumors, etc.

In another preferable embodiment of the present invention, the cancer patients are those who donated or those who did not donate the tumor cells for the manufacture of the cell populations with anti-tumor immune response activity by the method.

In another preferable embodiment of the present invention, the cancer patients are those who donated or those who did not donate the mononuclear cells to prepare the cell populations with anti-tumor immune response activity by the method.

Other aspects of the invention will be apparent to the skilled in the art in light of the technical disclosure of the invention.

FIGURE DESCRIPTION

FIG. 1 showed that the tumor cells were in close contact with the mononuclear cells in the same three-dimensional cell culture device.

Figure 2:
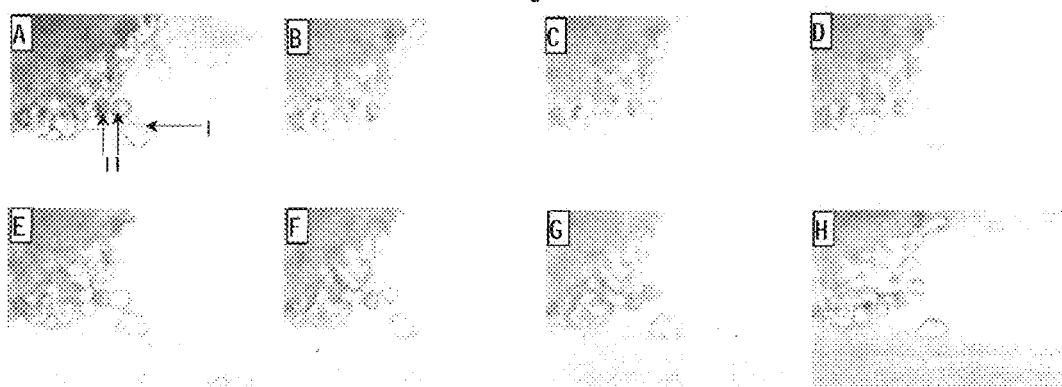

FIG. 2 showed the antigen collecting and the transfer process of the mononuclear cell.

Figure 3:
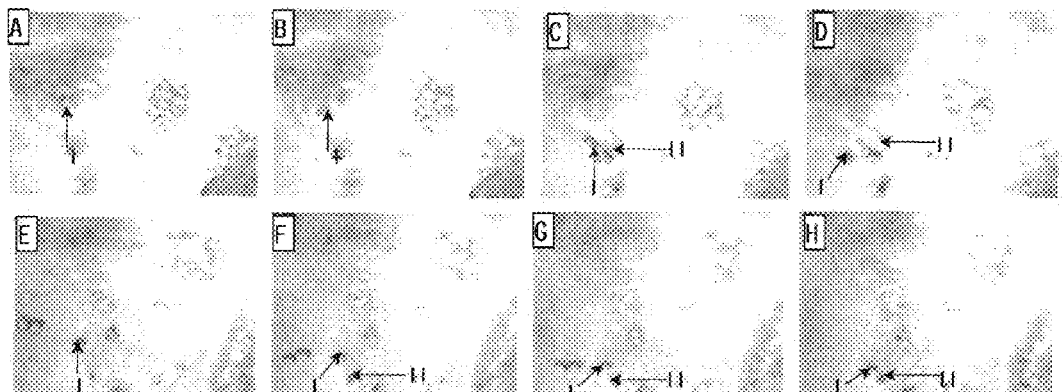

FIG. 3 showed the course in which the dendritic cells activate the mononuclear cells.

Figure 4:
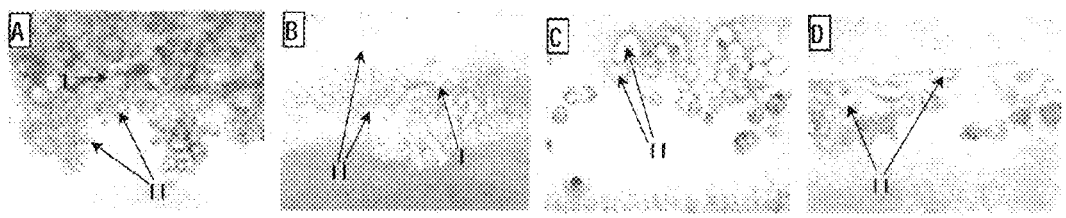

FIG. 4 showed that a large number of proliferations and differentiations of the mononuclear cells could be realized when it was being cultured with the tumor cells in the same three-dimensional cell culture device.

Figure 5:
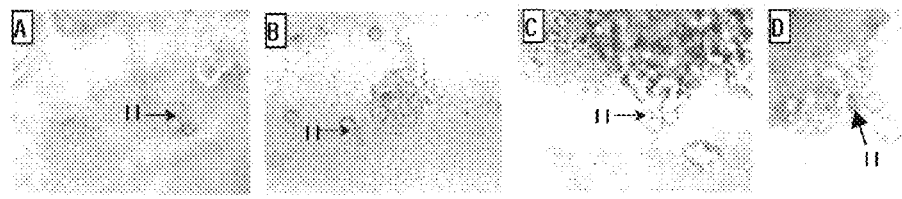

FIG. 5 showed that two or three mature mononuclear cells move together to form two or three-cell units, and thus it can cooperate with each other to implement the functions of the cell.

Figure 6:
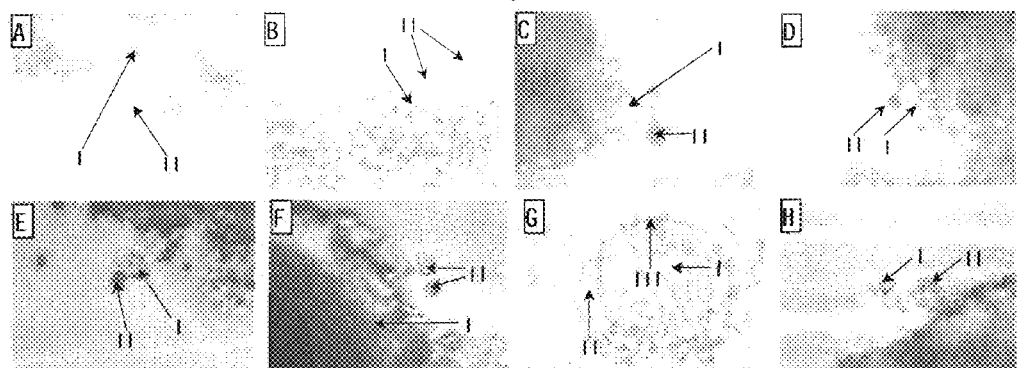

FIG. 6 showed the anti-tumor effects of the sensitized cell populations with the anti-tumor immune response activity.

Figure 7:
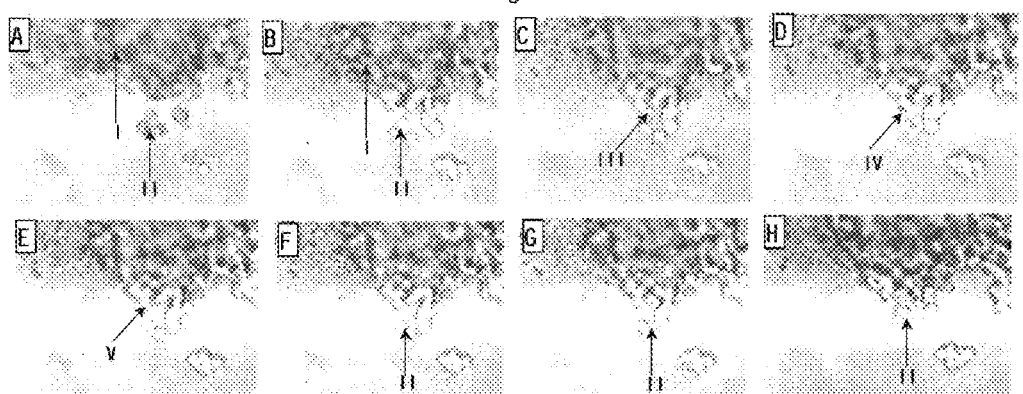

FIG. 7 showed the anti-tumor metastasis effects of cell populations with anti-tumor immune response activity.

Figure 8:
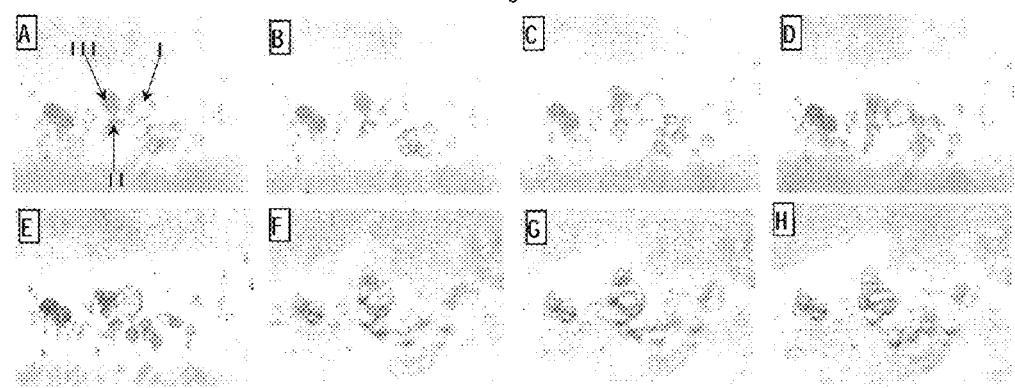

FIG. 8 showed the course in which the cell populations with anti-tumor immune response activity killed tumor cells.

Figure 9:
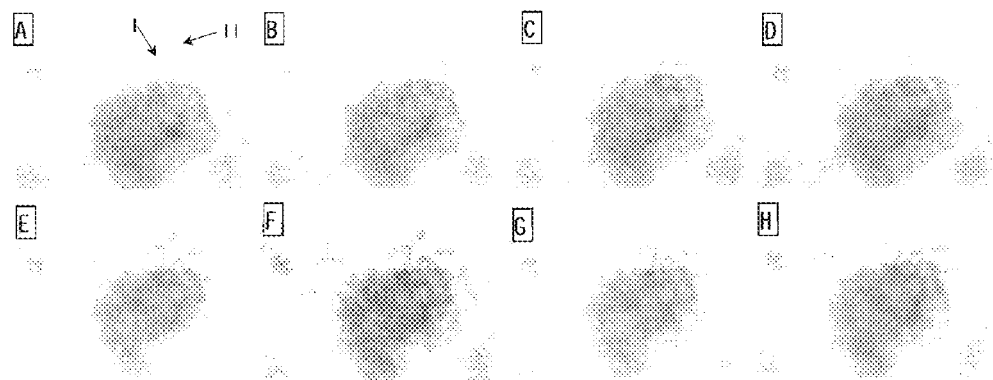

FIG. 9 showed the course that cell populations with anti-tumor immune response activity could lysis liver cancer cells.

Figure 10:
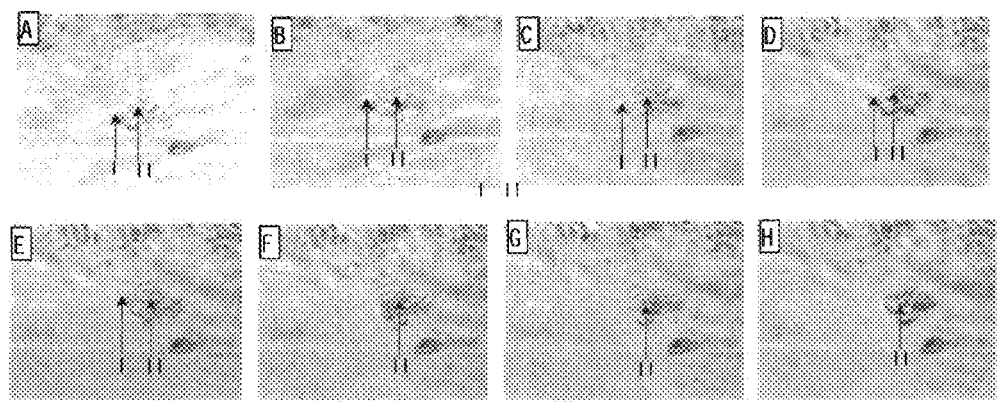

FIG. 10 showed the roles played by macrophages in killing tumor cells in the malignant pleural effusion.

Figure 11:
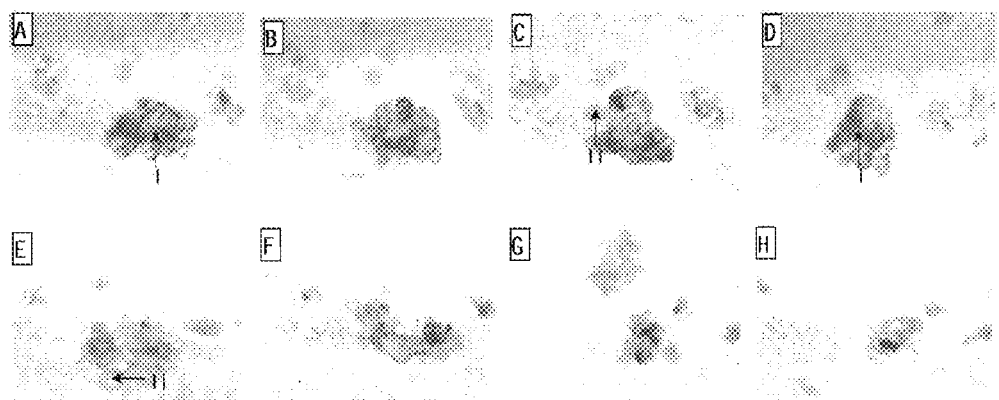

FIG. 11 showed the cell populations with anti-tumor immune response activity attacking tumors.

Figure 12:
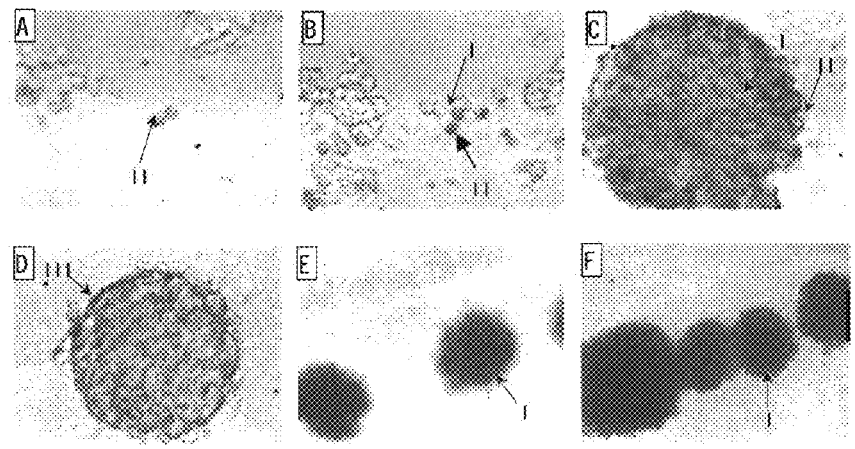

FIG. 12 showed the effects of the cell populations with an anti-tumor immune response activity sensitized by colon cancer cell lines later in contact with the colon cancer cells again.

Figure 13:
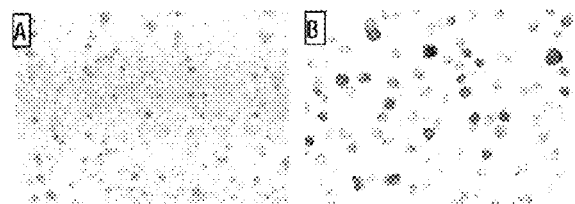

FIG. 13 showed the sensitized cell populations with anti-tumor immune response activity in the two-dimensional medium.

Figure 14:
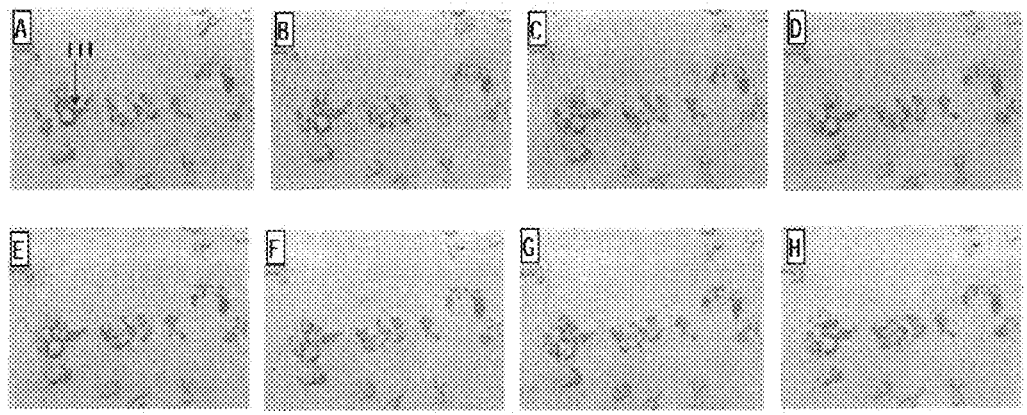

FIG. 14 showed the dendritic cells obtained by the method. As shown in the figure, the morphology of the dendritic cells is similar to that of matured dendritic cells, with good mobility.

Figure 15:
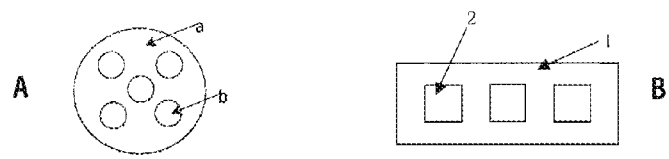

FIGS. 15A and 15B showed respectively the sketch map of the cross section of the three-dimensional culture unit in the preferable embodiment of the present invention.

MODE OF CARRYING OUT THE INVENTION

After extensive and intensive studies, the inventors of the present invention invented a method to prepare cell populations with anti-tumor immune response activity. The method of the present invention mainly aims to improve the antigenicity of tumor cells, enhance the sensitization of mononuclear cells, and promote the differentiation and proliferation of the cells, while at the same time enhancing the biological effects of sensitized immune cells. By means of said method, a large number of sensitized cell populations with high anti-tumor immune response activity can be obtained within a short period of time. On basis of this, the present invention is completed.

As used herein, the term "cell populations with anti-tumor immune response activity" is referring to the sensitized cell populations with anti-tumor immune response activity derived from mononuclear cells (which can be obtained from the peripheral blood of cancer patients and healthy donors) after the mononuclear cells have contact with and are sensitized by tumor cells (such as tumor tissues, malignant ascites or pleural effusions or cancer cell lines). In generally, it includes tumor-infiltrating lymphocytes (TIL), lymphokine-activated killer cells (LAK), natural killer cells (NK), tumor-associated macrophages (TAM), activated killer monocytes (AKM), cytotoxic T lymphocytes (CTL) and dendritic cells (DC). The cell populations with anti-tumor immune response activity can also be named as a kind of "cancer vaccine"; more specifically, it can be named as "therapeutic cancer vaccine" which can be used to treat cancers. The "cell with anti-tumor immune response activity" is referred to the individual cell as the "cell populations with anti-tumor immune response activity".

As used herein, the term "sensitized cell with anti-tumor immune response activity", the "the cell with anti-tumor immune response activity" and "the immuned cell" or "the sensitized cell" are interchangeable.

As used herein, the "mononuclear cell" is referred to as the cells with anti-tumor effects, and in general it can be obtained from the peripheral blood (from either cancer patients or healthy donors), or from the tumor tissues, malignant ascites, or malignant pleural effusion of cancer patients by means of discontinuous density gradient centrifugation. The cells with anti-tumor effects mainly include lymphocytes, monocytes, basophilic cells, etc. DC can also be obtained from the hematopoietic stem cells in the bone marrow.

The tumors, tumor cells and mononuclear cells adopted by the present invention may be autologous or allogenic.

Three-Dimensional Cell Culture Device

As used herein, "three-dimensional cell culture system", "three-dimensional culture system", "three-dimensional spacial culture system", "three-dimensional culture device", "three-dimensional spacial cell culture device", "three-dimensional cell culture device" and "three-dimensional spacial culture device" are interchangeable, and all of them are referred to as the three-dimensional cell culture system which is used to culture cells and provide them with a growth environment which is similar to an in vivo growth environment. This concept can be extended to the spheriform multicellular tumor culture system.

The present inventors co-culture tumor and mononuclear cells in a three-dimensional culture device, the device includes:

(a) a container with liquid cell culture medium; and (b) a three-dimensional cell culture unit in the liquid cell culture medium, said unit includes the empty cavities which are used for cell culture and the empty cavity walls which are used to define the empty cavities; the empty cavity walls contain biodegradable materials by which cells can adhere and grow, in addition, some substances such as nutritional ingredients and the products of cell metabolism can permeate the empty cavity walls.

In another preferable embodiment of the present invention, the empty cavity walls contain 80-100 wt % biodegradable materials.

In another preferable embodiment of the present invention, the cross-sectional area, length and thickness of the empty cavity are 0.1-100 mm$^2$, 1-1000 mm and 0.1-10 mm, respectively. In another more preferable embodiment of the present invention, the thickness of the empty cavity wall is 0.1-6 mm; and more preferably, it is 0.1-2 mm.

In another preferable embodiment of the present invention, the liquid cell culture medium can permeate the empty cavity walls.

In yet another preferable embodiment of the present invention, the biodegradable materials will melt at relatively high temperatures (50-100° C.), while it is in a solid form at room temperature (25-37° C.), or in a liquid form at a low temperature (4° C.) and solidified at room temperature (25-37° C.), respectively. The biodegradable materials are gels which are made of biodegradable substances which are selected from agar, agarose, hydrogels, collagen and matrigel, or their combinations. Preferably, it is nonopaque, transparent and semitransparent.

The biodegradable substances are soluble in 50-99.99% water, physiological saline solution, PBS, or cell culture medium containing extracellular matrix, growth factors, hormones and vitamins.

The shapes of the empty cavities in the invention are not limited in a particularly way and various shapes which are suitable for the culture, contact and the interaction of tumor cells and mononuclear cells can be adopted.

Other characteristics of the three-dimensional cell culture device can also be found in the inventors' Chinese patent application 200610023537.5 or PCT patent application PCT/CN2006/000432.

Tumor Culture

The tumor cells used in the present invention can be obtained from a variety of sources such as tumor tissues, malignant ascites and malignant pleural effusion; in addition, a certain number of tumor cells can also be obtained by culturing the existing various tumor cell lines.

The three-dimensional cell culture device can simulate the internal environment to prepare a solid tumor model in vitro, and the cell biological characteristics of the constructed tumors are similar to those of malignant tumors in vivo. Moreover, it can secrete tumor-associated antigens. The method can be used to observe the characteristics of tumor cells such as growth, migration, movement, invasion, metastasis, apoptosis, etc. at any time. The tumor model provides a unique environment for the study of cancer, and with it, various basic and clinical researches on designated tumors can be carried out.

The tumors are selected from: nasopharyngeal cancer, esophageal cancer, gastric cancer, liver cancer, breast cancer, colorectal cancer, prostate cancer, lung cancer, cervical cancer, leukemia, cancer in the oral cavity, salivary gland tumors, nasal cavity and nasal sinus cancer, laryngeal cancer, ear cancers, eye cancers, thyroid cancer, mediastinal tumors, chest wall and pleural tumors, intestinal tumors, biliary tract cancer, pancreatic and periampullary tumors, mesenteric and retroperitoneal tumors, kidney tumors, adrenal tumors, bladder tumors, prostate cancer, testicular tumor, penile cancer, endometrial cancer, ovarian cancer, malignant trophoblastic tumor, vulvar and vaginal cancers, malignant lymphoma, multiple myeloma, soft tissue tumors, bone tumors, skin and accessories tumors, malignant melanoma, nervous system tumors and pediatric tumors.

Other characteristics of tumor culture can also be found in the inventors' PCT patent application PCT/CN2006/000432.

The Co-Culture and the Separation of Mononuclear Cells and Tumors

The present invention provides a method for preparing cell populations with anti-tumor immune response activity, which includes: (1) co-culturing tumors and mononuclear cells in a three-dimensional cell culture device so as to obtain the cultures comprising the cell populations with anti-tumor immune response activity; (2) separating the cell populations with anti-tumor immune response activity from the cultures.

In the present invention, in order to obtain the sensitized cell populations with anti-tumor immune response activity, the proportion of effector cells and tumor cells is usually (5-100):1; preferably, (5-50):1; and most preferably (10-25):1. However, the proportion of the cell populations with anti-tumor immune response activity and the tumor cells may be different according to the different kinds and the different tissue types of malignancy of tumors; the skilled in the art can determine appropriate proportion by testing and evaluating the characteristics of the tumors.

In the present invention, the co-culture time of tumor cells and mononuclear cells is 3-60 days (more preferably, 7-28 days and most preferably, 14-21 days). A large number of sensitized cell populations with anti-tumor immune response activity can be obtained in the culture period. Generally, 14-21 days after culturing cells, $1\times10^5$-$1\times10^{11}$ cell populations with anti-tumor immune response activity can be obtained depending on different concentrations of initial cells.

By means of the method, the mononuclear cell stimulated by tumor antigens can excrete IL-2 or other cytokines in the course of co-culture, so the dependency of mononuclear cell on IL-2 is relatively low and even does not need IL-2. Exogenous IL-2, of course, can be added into the culture medium while the cells are being cultured, which can promote further the proliferation of activated T lymphocytes. For example, the exogenous IL-2 can be added to a concentration of 90-10000 IU.

A large number of cells with anti-tumor immune response activity comprised in the cultures can be separated by the conventional methods in the art. The method of separation adopted by the present invention has no special limit. For example, it can be separated by discontinuous density gradient centrifugation or by designing a kind of culture condition suitable for the cells with anti-tumor immune response activity that allows it to grow while limiting the growth of tumor cells so it would remove tumor cells and preserve the cells with anti-tumor immune response activity (for example, to culture the TIL cells in a two-dimensional culture system). Similarly, the conventional methods in the art can also be used to amplify the cells with anti-tumor immune response activity, which includes amplifying cells in the bioreactor.

To Improve the Antigenicity of Tumor Cells

In the present invention, the tumors or tumor cells are cultured within a three-dimensional cell culture device to improve the antigenicity of tumor cells. The biological characteristics and the gene expression of solid tumors in vivo can be mimicked by the tumor cells in vitro which are cultured in the three-dimensional cell culture device. Therefore, the antigenicity of the tumor cells can be enhanced or improved. Compared with other existing methods, the three-dimensional cell culture device can provide mononuclear cells (immune cells) with an environment similar to a cell-mediated immunity environment in vivo, and provide a target of tumors similar to solid tumors in vivo, thus improving the quality and quantity of tumor antigens. These antigens are not merely referred to as inactivated cells, the cleavage products of cells, proteins, peptides or other antigen components. In fact, they are very similar to the antigens of living malignant tumors.

It is known that polypeptide antigens do not always induce the best anti-tumor immune response, but the antigens of living tumor cells adopted (preferably by the present invention) can induce comparatively superior anti-tumor immune responses. It is not necessary to know tumor antigens in the production environment of the cell populations with anti-tumor immune response activity in the present invention; the tumor antigens can be acquired by mononuclear cells themselves. In addition, although MHC-I restricted antigenic peptide can be obtained and separated from tumor cells effectively by making use of extracts to stimulate DC, it needs a large number of tumor tissues and the components of the extract are complex. Moreover, the remaining normal antigens of body will lead to the potential risk of autoimmune. All these disadvantages can be overcome by established tumor cell lines.

Integrated tumor cells and living tumors all have complete antigenicities, so the immune effect induced by them can target various antigens at same time. The three-dimensional culture system not only can ensure tumor cells to express fully the tumor antigens with heterogeneities, but also can provide the environment for co-stimulatory factors and cytokines which are necessary for the activation of antigens. Moreover, it will be helpful to overcome possible adverse environments inside the body. By means of eliminating irrelevant substances which may inhibit immune responses and remove negative regulation on immune cells and break immune tolerance, the quality of tumor vaccines produced will be improved as well.

The present inventors make use of autologous or allogenic tumor cells to carry out immunoreactions in vitro, and then separates sensitized mononuclear cells from tumor cells with the established method. Moreover, due to the tumor cells being killed gradually in the course of the culture, cell populations with anti-tumor immune response activity (which can be made into cell vaccine) aimed at specific tumors can finally be obtained at the end of cell culture. The method of the present invention can not only fully retain the immunogenicity of tumor cells, but also can overcome "blindness", which will be helpful to improve the efficacy of immunotherapy.

Whether or not the functions of antigen-presenting cells (which process and present the tumor antigen initially) can be realized determines, to a large extent, the anti-tumor immune effect of cancer vaccines. The immune cells in the three-dimensional environment provided by the present invention can seek for tumor cells, capture the antigen, and activate anti-tumor effects by themselves. The close and effective contact between mononuclear cells and tumor cells at the early stage of cell culture, combined with the environment of cell-mediated immunity similar to the in vivo environment, as well as an effective antigen presentation, lead to a large number of sensitized immune cells with anti-tumor immune response activity being produced.

The activation of mononuclear cells needs tumor-specific antigens or tumor-associated antigens to present antigens. Moreover, it is necessary for mononuclear cells to contact with tumor cells early and regularly so as to maintain its activity of cell proliferation and specific killing effect towards the tumors and to increase the number and anti-tumor activity of effector cells. The mononuclear cells in the three-dimensional culture device can capture antigens continuously in the course of the progression and development of the tumors. A long-term cell culture can ensure mononuclear cells contact with tumor cells, which can make tumor cells express tumor antigens continually and to stimulate immune cells repeatedly. This process of antigen capture will be helpful to overcome the escape phenomenon of tumors.

To Improve the Sensitization of Immune Cells and Promote their Differentiation and Proliferation The mononuclear cell can exert fully its functions by means of the three-dimensional culture system. Only by MHC molecules presenting tumor-associated antigens for appropriate T cell subsets, can T cells be activated in the micro-environment with co-stimulatory factors and cytokines. Therefore, it is necessary for a successful anti-tumor immunogen to produce or trigger a local or regional activated micro-environment that is helpful for antigen-presenting, and T cell activation and proliferation. However, the establishment of such a micro-environment needs the participation of "professional APCs". Mononuclear cells, by means of cell-mediated immunity which is similar to the environment in vivo, can identify and capture antigens effectively; for example, macrophages and dendritic cells can transmit, digest, and present antigens so as to induce the differentiation and proliferation of a large number of cells with immune activity. The recognition of T cells on target cells is a precondition for various immune cells to coordinate cell-mediated immunity and to fully exert anti-tumor effects (such as mobilizing the anti-tumor effects of immune organs, immune cells, and immune molecules) and then a series of effective biological immune responses and anti-tumor effects can be fully developed.

The present inventors have found that in the course of immune response, that is the generation of activated mononuclear cells that attacks and kills the tumor cells. The mononuclear cells play a cooperative role, and thus the cancer vaccine prepared by the present invention includes various cell populations with anti-tumor immune response activity which is relevant with cell-mediated immunity. A variety of immune cells cooperate with each other to form a comprehensive, effective, and lasting anti-tumor immune response. The biological effects triggered by the joint cooperation of various immune cells fully demonstrate the importance of joint coordination between immune cells or between immune cells and other immune cells. Combined adoptive cellular immune therapy and vaccine specific immune therapy, for example, can induce sensitized tumor-specific T lymphocytes easily, and thus improve the efficacy of transferred effector cells. In addition, there is an immune-enhancing effect between cytotoxic effector cells (CTL, NK, macrophages, etc.) and secreted factors on killing tumor target cells, which is the basis of a by-stander killing effect. The secretion of cytokines and an appropriate ratio of different cytokines are important to enhance immune effects.

Sufficient immune cells with specific anti-tumor effects can be obtained at an early time of cell culture, by using the three-dimensional cell culture system. This system can also ensure various antigens with different heterogeneities to induce immunity at one time, thus improving the quantity of the immune cells. The anti-tumor immune response induced by the method of the present invention contains not only CTL clones with a single epitope (which may not able to induce an effective anti-tumor effect), but also CTL clones with multiple epitopes. That means it can induce polyclonal responses namely $CD8^+$ and $CD4^+$ T cell responses which target various tumor antigen epitopes. The best anti-tumor effect may be obtained by means of the joint coordination of these cells. The present invention can make use of polyclonal or antigen-specific immune cells to identify and kill tumor cells. Moreover, it can choose lymphocyte subsets which are more sensitive to tumor cells and amplify them in vitro.

In the present invention, tumor cells and mononuclear cells are co-cultured in the three-dimensional cell culture system and the cell proliferation and differentiation of mononuclear cell can be achieved within 7-10 days of the culture. A large number of activated immune cells (cells with anti-tumor immune response activity) obtained at the early time of cell culture may survive for a long time after it was transferred into the body of the recipient. Moreover, the specific anti-tumor effect can be maintained for a period time. These immune cells will amplify rapidly and effectively when it is stimulated by tumor antigens again, and thus a specific anti-tumor immune response can be mediated by them and finally lead to tumor rejection. Since these immune cells have a long life-span and will proliferate for a long time in the body, it will be helpful to obtain a long lasting immune effect.

The method provided by the present invention is a simple, convenient, ideal and natural way which accords with the normal physiological processes of the body, not needing the introduction of viruses and a modification in genes. The activated immune cells obtained by the method are autologous or allogenic, which is helpful for the preparation and clinical application of the cancer vaccine.

To Enhance the Biological Effects of Immunocompetent Cells

The immune cells obtained by the method of the present invention show their immunological activity at the early days of cell culture, and it can survive several months. The course that immune cells capture, digest and transmit tumor antigens can be observed in vitro. In addition, the cancer vaccine has various powerful immunological effects such as preventing the growth and metastasis of tumor cells, lysis, and phagocytosing tumor cells directly.

The sensitized cell populations with anti-tumor immune response activity obtained by the present invention can carry out immune surveillance and prevent the metastasis and the proliferation of tumor cells. It will attack and kill the tumor cells once they metastasis to other places; sometimes, the cell populations with anti-tumor immune response activity will form capsule at the edge of tumors, a morphological feature similar to benign tumors.

The examples of the present invention demonstrated that the tumor cells were dissolved completely within several minutes after it had contact with small sensitized lymphocytes. The effect and the course of macrophage killing tumor cells shows that it had contact with tumor cells first; and then, after a certain period of time, (which may be a phase that macrophages triggered and activated an immune response), tumor cells are finally phagocytosed. The present inventors also observed that an autologous tumor was attacked by sensitized cell populations with anti-tumor immune response activity in vitro, and as a result, the size of it reduced obviously and the tumor disappeared. In addition, the present inventors found that the killing effect of immune cell populations on tumor cells was associated with the reduced tumor-associated antigen. In an example of the present invention, under the condition of the three-dimensional culture, the concentration of alpha-fetoprotein in the liver cancer cell line ATCC-HB 8065 culture medium without peripheral blood mononuclear cells was 1000 ng/ml, but it decreased to 51.72 ng/ml in the culture medium when peripheral blood mononuclear cells were added, which was reduced by 20 times. Similarly, it was 65.43 ng/ml in the culture medium of Lovo colon cancer cell lines control sample (without peripheral blood mononuclear cells) and decreased to 11.33 ng/ml in the culture medium of the treated sample (with peripheral blood mononuclear cells) respectively, the latter reduced by 6 times.

The cell populations with anti-tumor immune response activity provided by the present invention includes integrated functions, namely active specific, active non-specific, passive specific, and passive non-specific immunities, which provides a comprehensive treatment strategy for the biological treatment of tumors. Combined with a humoral immune system, better biological effects may be obtained further in the clinical treatments, including the effect on the tumor cells at quiescent cell cycle, drug-resistant cells and even on cancer stem cells.

The morphological characteristics of dendritic cells obtained by the present invention are similar to mature dendritic cells. Moreover, it has a good motility. It is observed that dendritic cells depart from the tumor (obtain the antigen from the tumor), then move to adjacent mononuclear cells and have contact with them (activation). The dendritic cells with tumor-associated antigens can break immune tolerance and bring about the cytotoxic immune response of anti-tumor cell; at the same time, the immune escape of tumor cells can be avoided. Immune cells can amplify rapidly and effectively, mediating specific anti-tumor immune effects and leading to tumor rejection once there is contact with tumor antigens again. The dendritic cells obtained by the method of the present invention can be used to prevent various solid tumors, which will help eventually cure human cancers.

At present, many aspects of the interaction between tumor cells and immune cells are still unclear, but the present inventors have established an ideal model to observe biological therapy of tumors in vitro. By using the three-dimensional cell culture system, we can realize a real time observation and have a dynamic understanding of the mechanism of various phases of immune cells, namely the initiation phase, differentiation-inducing phase, and biological effects phase. For example, we can observe and understand a series of key processes such as the acquisition, process and transfer of antigens, study the effective mechanism for the activation of T cells (such as co-stimulatory factors) in the environment which is similar to a cell-mediated immunity environment in vivo, observe and study the mechanism of immune escape of tumor cell under a controllable condition, and observe biological effects brought about by immune cells on tumor cells such as immune response effect, immune monitoring and objective tumor regression. The method can also be used to separate, screen, identify and synthesize artificially tumor antigens. Moreover, it can be applied to research the immunogenicity of tumor antigens and improve the preparation of cancer vaccine at cellular, molecular and gene levels.

The cell populations with anti-tumor immune response activity obtained by the method of the present invention can be used for active specific immunotherapy. The present inventors, based on the theoretical basis of active specific immunity, provide a new method to study tumor vaccines to improve its specificity, safety and efficiency: 1) culture immune cells in the three-dimensional environment so as to make it to seek for tumor antigen spontaneously, 2) prepare tumor vaccines under a controllable condition in vitro (modification of cytokines, immune adjuvant, immune regulator), which can break the body's immune tolerance on tumors, relieve immunosuppression, and avoid or overcome T cell anergy, 3) through the cooperative effect between various immune cells, the comprehensive anti-tumor effect of cell-mediated immunity can be enhanced, which includes that tumor cells are dissolved directly by $CD8^+$ CTL; the direct killing effect of tumor cells such as tumor cells be digested by various enzymes. Moreover, $CD4^+$ T cell can release cytokines to kill tumor cells or inhibit their growth indirectly or directly.

The method invented by the present inventors overcome various current restrictions on the clinical application of DC: 1) by means of the method provided by the present inventors, macrophages and lymphoid toxic cells can kill and lysis tumor cells so as to provide various suitable tumor antigens for DC; 2) the MHC restriction can be avoided by adopting autologous DC; 3) in the production environment of a cancer vaccine, the present inventors do not always need to know tumor antigen, in fact, immune cells can capture tumor antigens independently; 4) it is known that the best anti-tumor immune response can not always be induced by polypeptide antigens alone, however, the antigens of the living tumor cells adopted by the present inventors can induce an ideal anti-tumor immune response; 5) the method provided by the present invention not only targets single epitope CTL clones, which may not able to induce an effective anti-tumor effect, but also can obtain CTL clones with multiple epitopes; the best anti-tumor effect can be realized by means of the combined effect of these cells. In addition, although MHC-I restricted antigen peptide separated and obtained from tumor cells has certain effects, the method that makes use of extract to stimulate DC needs a lot of tumor tissues. Moreover, the antigen of extract has complex components and there is a potential risk that the normal antigens of body will lead to autoimmunity. All these disadvantages can be overcome by established tumor cell lines.

The method adopted by the present inventors is that making sure of the antigens of tumor cell to activate immune cells, which differs from the method that involves activating TIL with IL-2 alone. This method can ensure tumor cells contact with immune cells at the early stage of the cell culture, and combined with the mediated role played by other T cell-associated molecules, the effective tumor tumor-specific antigen or tumor-associated antigen can be provided. In the course of long-term cell culture, immune cells closely contact with the tumor so as to maintain its activities, namely cell proliferation and a specific killing effect on autologous tumors, through a specific activation mechanism. Since the T cells activated by this mechanism can excrete IL-2 and other cytokines when it is stimulated by antigens, it shows a lower dependence on IL-2 and the amount of IL-2 to be added is small. The T cell can survive for a long time and maintain its specific anti-tumor immune response after it was infused into the body of the recipient. Moreover, it can amplify rapidly and effectively, mediate specific anti-tumor immune response, and reject the tumor once it is stimulated by tumor antigen again.

Theoretically, making use of sensitized tumor-specific T lymphocytes to treat tumor has great advantages, which has been proved by animal experiments; however, it is still very difficult to apply it in the clinical treatment due to several technical reasons. The method provided by the present inventors overcame existing difficulties, which has advantages as follows: 1) high frequency of effector cell precursors and timesaving in vitro culture and amplification with low cost, 2) the antigenicity of tumors in the course of evolution changes frequently (such as antigen modulation), which will lead to some tumor cells to escape from the attack of T lymphocytes and grow continuously, and thus become the seeds of the recurrence and metastasis of tumor; the sensitized cells in the system provided by the present inventors can react continuously with the tumor cells, which can produce corresponding immune responses for changed tumor cells to avoid tumor escape, 3) immune response can be induced by autologous immune cells to overcome the MHC restriction on the anti-tumor effect of T lymphocytes, which may not be realized by allogenic T lymphocytes.

The method provided by the present inventors overcame many restrictions or shortcomings of LAK/IL-2 therapy such as the small number and the low amplification of LAK precursors and the need of taking a large number of leukocytes from the body, which will lead to infection easily and weaken the body's immune system. In addition, the immunosuppression brought about by the growth of the tumor lead to poor quality of LAK cells induced by patient's leukocytes—all these defects above can be overcome by allogenic mononuclear cells. Since the method belongs to non-specific immune response, it has a limited killing effect. Applying high-dose IL-2 repeatedly will frequently cause serious side effects which will make patients unable to tolerate treatment; the method used by the present inventors, however, includes various mechanisms. A large number of mononuclear cells produced by the method can excrete endogenous IL-2, which can improve the in vitro culture and the inducement of LAK cells; it can improve efficacy and reduce treatment cost, and thus make this LAK/IL-2 therapy more accepted by the patients.

The biggest problems of TIL/TDAK therapy are as follows: 1) cell culture is very time-consuming, laborious, expensive and easily contaminated, which is more obvious than that of LAK cells, 2) the activity of TIL rests with the tumor's type, size and the degree of necrosis; not all tumors can be infiltrated by lymphocytes, 3) the proliferative and anti-tumor activities of TIL will reduce with prolonged culture time; apoptosis can be found in some cells in the course of cell culture, 4) it is difficult to obtain self-tumor-specific TIL from most tumors; moreover, the TIL obtained from metastatic tumors or tumors which can secrete immunosuppressive factors may not be amplified in vitro; the tumor infiltrating lymphocyte has diversity, which is determined by the immunity of tumor cells. The anti-tumor effect of TIL will be diminished by the abnormal differentiation and the shortage of cytokine or tumor free components which are necessary for TIL to exert killing effects. The biggest challenge faced by TIL cell therapy is how to obtain a large number of early effectors to carry out adoptive cell-mediated immunotherapy, which has been overcome by the present inventors. By means of the method provided by the present inventors, a large number of early stage anti-tumor immune active cells can be obtained within 2-3 weeks, which is far less than that of a TIL cell culture (in general, the culture time is 45-60 days).

The three-dimensional cell culture system can also be used to prepare various cancer vaccines such as embryonic antigen vaccines, virus vaccines, cancer gene products, synthetic peptide vaccines, anti-idiotypic antibody vaccines and genetically engineered vaccines. At the same time, it is helpful for the study of immune adjuvants such as non-specific immune adjuvants, the gene modification of tumor cells and peptide-assisted T helper cell immune response; moreover, it can offer co-stimulatory signals and cytokines for T lymphocytes and present the antigens which are coded by recombinant plasmid and the bacterial or virus.

In addition, the present invention also provides a kit which includes a container; the container comprises the cell populations with anti-tumor immune response activity obtained by the method. The number of the cell populations in the preferred embodiment of the present invention is $1\times10^5$-$1\times10^{11}$. At last, various existing methods in the art can be used to transfer the cell populations into an infusion solution such as 40 ml 25% normal serum albumin and 160 ml normal saline. More preferably, the container also includes an operation manual.

The present invention also provides a use of the cell populations with anti-tumor immune response activity obtained by the method; it can be used to prepare cell therapy drugs for tumor.

The present invention also provides the methods for the treatment of tumors, it includes infusing the cell populations with anti-tumor immune response activity obtained by the method into cancer patient's body, wherein, the cancer patient may be or may not be the patient who donates tumor cells for the method of the present invention. The cancer patient may be or may not be the patient who donates mononuclear cells for the method of the present invention.

The dosage and administration route of the cell population with anti-tumor immune response activity should be chosen according to the patient's individual characteristics and the degree of disease; for example, infusing the $1\times10^5$-$1\times10^{11}$ anti-tumor immune cells in to patient's body for about 7 days, every other 1-3 weeks. Of course, specific dosage should be decided by means of other factors such as administration route, health status, etc., and all these skills are not beyond the scope managed by skilled medical doctors.

The method of the present invention can be used alone; it can also be combined with other tumor therapies. The tumor therapies include, for example, surgery, chemotherapy, radiation therapy and other biological therapies.

The method provided by the present invention may play an important role in the prevention and the treatment of other diseases such as infection, immunodeficiency, autoimmune disease, etc., and even in the areas of transplant rejection and anti-aging therapy.

The present invention will be further illustrated with the following examples. It should be understood that, these examples are exemplary only and are not intended to limit the scope of the present invention. The experimental methods in the following examples not indicating the specific experimental conditions are typically carried out under the conventional conditions, for example, those in Sambrook, et al. Molecular cloning: A laboratory manual (New York: Cold Spring Harbor Laboratory Press, 1989), or following the manufacture's instructions. Unless otherwise indicated, all the percents and parts are calculated by weight.

General Materials and Methods

1. Construction of Three-Dimensional Culture System

To construct a three-dimensional culture system, the three-dimensional culture system includes: a container with liquid cell culture medium and three-dimensional cell culture units in the liquid cell culture medium, in which the three-dimensional cell culture unit has an empty cavity and empty cavity walls which are used to define the empty cavity, the empty cavity walls contain biodegradable materials on which cells can adhere and grow, and moreover, nutrients components and cell metabolites can pass through the empty cavity wall.

(1) In a preferable method, the empty cavity walls of the three-dimensional cell culture units are made of 1% agarose, and the cross-section of it is circular or approximately circular. A circular mold with a jacket pipe (external diameter: about 6 mm, length: about 200 mm) is used to prepare the three-dimensional cell culture units. 5 round wires (diameter: 0.3 mm, length: 300 mm) are arranged evenly in the internal cavity of the mold, which is filled with 1% agarose and after the agarose solidified, once taking out the wires and the mold, a three-dimensional cell culture unit (external diameter: about 5.8 mm) with 5 symmetrical internal cavities can be obtained. The sketch map of the cross-section is shown in FIG. 15A, wherein, a) denotes the empty cavity wall, b) denotes empty cavities. The three-dimensional cell culture units will be put into the liquid culture medium which is suitable for the growth of mononuclear cells and tumor cells.

(2) In another preferable method, the empty cavity walls of the three-dimensional cell culture units are made of 1.2% agarose; the cross-section of it is quadrate or approximately quadrate. Before preparing the three-dimensional cell culture unit, a cuboid mold with a metallic jacket pipe (length: 10 mm, width: 6.5 mm, height: 3 mm, the thickness of wall: 0.5 mm) is designed first; 3 quadrate wires (length: 20 mm, width: 0.9 mm, height: 0.9 mm) are arranged in the jacket pipe. The two ends of the jacket pipe are sealed with movable covers which are matched with the jacket pipe. After filling the mold with 1.2% agarose and taking out the wires and the mold after the agarose solidified, the three-dimensional cell culture unit (length: 10 mm, width: 5.5 mm, height: 2 mm) with 3 symmetrical internal cavities (0.9×0.9 mm) can be obtained. The sketch map of the cross-section is shown in FIG. 15B, wherein, 1) denotes the empty cavity wall and 2) denotes empty cavities.

The three-dimensional cell culture system can provide an environment which is similar to the cell-mediated immune environment in the body for the growth and the movement of tumor cells and mononuclear cells, which provides a perfect space and environment for them to contact or interact with each other.

2. The Separation of Mononuclear Cells (Non-Continuous Density Gradient Centrifugation)

The peripheral blood specimens (3 ml) anticoagulated by EDTA was collected by means of aseptic method, and cells were separated with lymphocyte separation medium (Ficoll-Hypaque, Sigma Inc) and non-continuous density gradient centrifugation. The concrete steps were as follows: adding 3 ml of 100% lymphocyte separation medium to the test tube, then adding 3 ml of a blood sample carefully on top of the solution, (along the wall of the test tube, these two parts of the solution should not be mixed), centrifugating it 25 min at 1500 r/min, collecting cells from the cell layer at the interface of the lymphocyte separation medium, and washing cells in turn with sterile buffer and RPMI1640 one time to obtain mononuclear cells. The actual number of specimens can be determined according to the number of cells which will be used.

The results from the test showed that the extracted mononuclear cells mainly include: mononuclear cells, lymphocytes, and basophilic cells.

Lymphocyte separation medium (density: 1.068) and non-continuous density gradient centrifugation can be used to separate DC.

3. The Extraction of Tumor Cell (Specimen)

A. From Malignant Pleural Effusion or Ascites

Tumor cells, conventionally, can be extracted from malignant pleural effusion or ascites, wherein, pleural effusion is suitable for the extraction of specimen of lung cancer and other secondary tumors, ascites is suitable for the extraction of specimens of digestive tract tumors, ovarian cancers, etc.

The patients, who, (confirmed by pathological cytology) suffered from malignant pleural effusion (such as lung cancer, breast cancer) or malignant ascites (such as colon cancer, liver cancer) can be enrolled to extract the specimens of tumor cells.

Taking pleural effusion or ascites 500-1000 ml from patients by means of aseptic method and pleuracentesis, the separation and preparation test, after adding heparin 10 U/mL into it, should be carried out immediately. One should centrifugate malignant pleural effusion or ascites with heparin 10 min at 1500 r/min (400 g). Then wash deposited cells with a sterile buffer twice to hemorrhagic pleural effusion or ascites, the concrete steps are described as follows: adding erythrocyte lysing solution (volume ratio: 1:10) into it and mixing it evenly; storing it at 4 C, 8 min; centrifugating it 5 min at 1500 r/min; washing deposited cells in turn with sterile buffer and RPMI1640 culture medium one time; suspending cells ($1\times10^6$/mL) in the RPMI1640 culture medium (containing 10% FBS) and putting it into the three-dimensional cell culture device for cell culture; the culture conditions: saturated humidity, 37 C, 5% $CO_2$.

B. Making Use of Tumor Cell Lines to Culture Tumor or Tumor Cell

By putting the selected cancer cell lines into the three-dimensional cell culture device described in "1" and adding appropriate culture medium into it to culture cells 3-7 days, then a certain number of tumor cells or micro-tumors can be obtained for use.

4. The Co-Culture of Tumor Cell and Mononuclear Cell in the Three-Dimensional Culture Device The tumor cells obtained from "3" are co-cultures with the mononuclear cells obtained from "2" in the three-dimensional culture device which was constructed by "1" mentioned above. The concentration of tumor cell and mononuclear cell is 5-50:1 (such as 25:1, namely, taking one tumor cell to activate 25 mononuclear cells so as to form a cancer vaccine), a preferable culture time is 14-21 days.

5. The Separation and the Culture of Sensitized Cell Populations with Anti-Tumor Immune Response Taking out the mixture of tumor cells and cell populations with anti-tumor immune response from the three-dimensional culture device, centrifugating it for 10 min at 1000 r/min, washing deposited cells with a sterile buffer twice and suspending it in buffer 3 ml; separating cells with lymphocyte separation medium and non-continuous density gradient centrifugation. The concrete steps were as follows: adding in turn of 100% and 75% lymphocyte separation medium 3 ml into the bottom and the middle-layer of test tube respectively; adding the cell suspension 3 ml carefully into test tube along the wall of test tube, which should not be mixed; centrifugating it 25 min at 2000 r/min (700 g) and collecting cell populations with anti-tumor immune response from 100% liquid interface. Centrifugating cell populations 5 min at 1000 r/min and washing deposited cells in turn with sterile buffer and RPMI1640 one time so as to obtain cell populations with anti-tumor immune response; transferring cell populations on a 6-well plate and culturing it for 48 h in an incubator (5% $CO_2$, 37 C); transferring them into a cell culture bottle and adding AIM-V serum-free culture medium (Gibco) with IL-2 1000 U/ml into the culture bottle.

6. The Culture and the Cell Proliferation of Cell Populations with Anti-Tumor Immune Response The cell populations with anti-tumor immune response can be proliferated further by means of suspending cells ($1.0 \times 10^6$/ml in the AIM-V serum-free culture medium with IL-2 1000 U/ml, which can be regarded as an optional way for cell proliferation. The cell populations can be cultured in the big culture bottles (175 cm$^2$) or culture bags (750 cm$^2$) so as to meet the need of large-scale culture for clinical treatment. Generally, subculture should be carried out once a week, which includes the replacements of fresh medium and rIL-2, adjusting cell concentration to $5.0 \times 10^5$/ml, and culturing them continuously in a new container. In addition, the cell populations with anti-tumor immune response can also be proliferated in a bioreactor.

Example 1

The Close Contact Between the Tumor Cells and Mononuclear Cells

Co-culturing liver cancer cell lines SMMC 7721 (Purchased from Cell Bank of Chinese Academy of Sciences) and peripheral blood mononuclear cells obtained from healthy donors in the three-dimensional culture unit (1) constructed by the method "1"; the composition of the culture medium includes: RPMI 1640 (Sigma Inc) 1000 ml, 100× penicillin+streptomycin (Gibco 15140-122) 10 ml and fetal bovine serum 100 ml. Culture condition: 37 C, 5% $CO_2$. Similar culture condition is used for colon cancer cell lines Lovo (Purchased from ATCC) and peripheral blood mononuclear cells obtained from healthy donors; the culture medium includes: 1000 ml Ham's F12K (Gibco 21700-026) culture medium with L-glutamine 2 mM, 100× penicillin+streptomycin (Gibco 15140-122) 10 ml, 10× glutamine 10 ml, fetal bovine serum 100 ml. Adjusting the concentration of mononuclear cells and tumor cells to 10:1, then observing the interrelationship between them by means of IX71 inverted microscope (Olympus).

The results showed that the mononuclear cells contacted closely with liver cancer cells and colon cancer cells within 24-48 h while they were cultured in the three-dimensional culture system. It is shown in the FIGS. 1A-D (liver cancer cells and mononuclear cells; 40×) and FIG. 1 E-H (colon cancer cells and mononuclear cells; E, F: 40×; G, H: 20×); in the figures, I denotes cancer cell, II denotes mononuclear cell.

Example 2

The Collection and the Transfer of Antigen by Lymphocytes

Adding colon cancer cell lines Lovo and peripheral blood mononuclear cells obtained from healthy donors into the three-dimensional culture unit (1) constructed by the method "1", then culturing it in the culture medium; the composition of the culture medium is same with that of example 1, adjusting the concentration of mononuclear cell and tumor cell to 10:1, then observing the interrelationship between them.

FIG. 2 A-H (40×) shows the phenomenon that at least two lymphocytes cooperated with the collection and the transfer of surface antigens of colon cancer cells at the 8$^{th}$ day of cell culture; wherein, the one lymphocyte captured antigens at the surface of tumor cell and the captured antigen was transferred by another one. FIGS. 2A-H showed the dynamic course of the collection and the transfer of antigens, which lasted 86 min; in the figures, I denotes colon cancer cells, II denotes lymphocytes.

Example 3

The Phenomenon that Dendritic Cell Activates Lymphocyte

Obtaining tumor cells and mononuclear cells from the malignant pleural effusion of a patient who suffered from lung cancer by means of the method; mixing the obtained cells with autologous peripheral blood mononuclear cells 3 ml and putting them into the empty cavity of three-dimensional culture unit (2) constructed by the method "1"; the composition of the culture medium includes: RPMI 1640 (Sigma Inc.) 1000 ml, 100× penicillin+streptomycin (Gibco 15140-122) 10 ml and fetal bovine serum 100 ml. Culture conditions: 37° C., 5% $CO_2$.

The results showed that dendritic cells, at the 9$^{th}$ day of culture, departed from tumors (extracted antigen from tumor) and moved to surrounding lymphocytes so as to contact with (activate) them. FIGS. 3A-H showed the dynamic course that dendritic cell activates lymphocytes, which lasted 94 min; in the figures, I denotes dendritic cells, II denotes lymphocytes.

Example 4

The Proliferation and the Differentiation of Mononuclear Cell

Co-culturing colon cancer cell lines Lovo and liver cancer cell lines SMMC 7721 respectively with peripheral blood mononuclear cells obtained from healthy donors into the three-dimensional culture unit (1) constructed by the method "1"; the methods of culture are same as the former method. The proliferation and the differentiation of mononuclear cells can be observed at 7-10$^{th}$ day of cell culture.

FIGS. 4A-B (A, 40×; B, 20×) shows the conditions of growth of colon cancer cells and mononuclear cells observed at the 7$^{th}$-10$^{th}$ day of cell culture in the three-dimensional culture device, from which a large amount of proliferation of mononuclear cells can be found. In the figure, I denotes colon cancer cells, II denotes mononuclear cells.

FIGS. 4C-D (40×) showed the conditions of growth of liver cancer cell and mononuclear cell observed at 14$^{th}$ day of cell culture in the three-dimensional culture device, the differentiation of mononuclear cells can be observed.

Example 5

The Congregation and the Cooperation of Mononuclear Cell

Obtaining tumor cells and mononuclear cells from the malignant ascites of patient who suffered from colon cancer by means of the mentioned method; mixing the obtained cells with autologous peripheral blood mononuclear cells 3 ml and putting them into the empty cavity of three-dimensional culture unit (1) constructed by the method "1"; then culturing the three-dimensional culture unit in the culture medium, the composition of the culture medium includes: 1000 ml Ham's F12K (Gibco 21700-026) culture medium with L-glutamine 2 mM, 100× penicillin+streptomycin (Gibco 15140-122) 10 ml, 100×glutamine 10 ml and fetal bovine serum 100 ml.

Co-culturing breast cancer cell lines (ATCC HTB-22) and peripheral blood mononuclear cells obtained from healthy donors in the three-dimensional culture unit (1) constructed by the method "1"; then culturing the three-dimensional culture unit in the culture medium, the composition of the culture medium includes: Minimum essential medium (Eagle) with 2 mM of glutamine and Earle's BSS (Gibco 11700-077), sodium bicarbonate 1.5 g/L, non-essential amino acids 0.1 mM, sodium pyruvate 1 mM, bovine insulin 0.01 mg/ml, 100× penicillin+streptomycin (Gibco 15140-122) 10 ml and fetal bovine serum 100 ml. Culture conditions: 37 C, 5% $CO_2$. Adjusting the concentration ratio of mononuclear cell and tumor cell to 10:1.

Similarly, culturing colon cancer cell lines Lovo and peripheral blood mononuclear cells obtained from healthy persons in the three-dimensional culture unit (1) constructed by the method "1".

The phenomenon that two or three mononuclear cells got together can be observed at 10-$14^{th}$ day of cell culture, see FIG. 5A (ascites specimen, 40×); FIG. 5B (the specimens of mononuclear cell and breast cancer cells, 40×); FIGS. 5C-D (the specimens of mononuclear cells and colon cancer cells, 40×).

From the results above, we can see that two or three mature mononuclear cells stay together and form a combined two-cells unit or a combined three-cells unit of mononuclear cells to cooperate with each to execute the cellular functions.

Example 6

The Anti-Tumor Effect of Sensitized Cell Populations with Anti-Tumor Immune Response Activity Co-culturing liver cancer cell lines (SMMC 7721) and peripheral blood mononuclear cells obtained from healthy donors in the three-dimensional culture unit (1) constructed by the method "1"; the methods of culture are the same as the former method. At the $7^{th}$-$14^{th}$ day of cell culture, a great deal of cells with anti-tumor effect adhered to and covered the surfaces or the edges of tumors to inhibit the growth and the metastasis of tumors; the sensitized cells could also form a "fence" to prevent the metastasis of the tumor cells, see FIGS. 6A-B (20×), or monitor the transfer of tumor cells at the edge of tumor, see FIGS. 6C-E (40×). Once tumor cells starts metastasis, the sensitized cells could move toward the tumor cells and block them from departing from the tumor, see FIG. 6E. In the figures, I denotes liver cancer cell, II denotes cell populations with anti-tumor immune response activity.

Obtaining tumor cells and mononuclear cells from the malignant pleural effusion of patients who suffered from lung cancer by means of the mentioned method; mixing the obtained cells with autologous peripheral blood mononuclear cells 3 ml, adding them into the empty cavity of three-dimensional culture unit (1) constructed by the method "1", then culturing the three-dimensional culture unit in the culture medium and observing the interrelationship between sensitized cells and tumor cells. On the $14^{th}$ day of cell culture, it can be observed that the cells with anti-tumor immune response activity were stationed at the edges of tumors and monitored the metastasis of tumor cells, see FIG. 6F (40×). In the figure, I denotes tumor cells, II denotes cells with anti-tumor immune response activity.

Co-culturing colon cancer cell lines Lovo and peripheral blood mononuclear cells obtained from healthy donors in the three-dimensional culture unit (1) constructed by the method "1", then culturing the three-dimensional culture unit in the culture medium and observing the interrelationship between sensitized cells and colon cancer cells; the methods of culture are the same as former methods. At the $14^{th}$ day of cell culture, it can be observed that metastasis tumor cells can also be killed by the cell populations with anti-tumor immune response activity, see FIGS. 6G-H (40×). Sometimes, the cell populations with anti-tumor immune response activity could form "capsule" at the edge of tumors, which led to malignant tumors to show the morphological characteristics similar to benign tumors, see FIG. 6G. In the figure, I denotes colon cancer cell, II denotes cells with anti-tumor immune response activity, III denotes capsule.

Example 7

The Anti-Tumor Metastasis Effect by Cell Populations with Anti-Tumor Immune Response Activity Co-culturing colon cancer cell lines Lovo and peripheral blood mononuclear cells obtained from healthy donors in the empty cavities of three-dimensional culture unit (1) constructed by the method "1", then culturing the three-dimensional culture unit in the culture medium and observing the interrelationship between sensitized cells and colon cancer cell; the methods of culture are same with former method.

On the $9^{th}$ day of cell culture, we observed the phenomenon in which sensitized cells block the gap at which tumor cell metastasis occurred. It can be showed in the FIGS. 7A-H (20×) in which sensitized cells moved to the place at which tumor cell metastasis occurred, then appeared to release a small lymphocyte and some substances yet to be identified (may be a kind of substance for the attachment) through a "pipeline" which is formed by some unknown substances around the tumor; then the small lymphocyte moved to and stationed at the edge of the tumor to prevent tumor cells from metastasis again. At the same time, three sensitized cells had also moved to and stationed at the gap at which tumor cells metastasis occurred. FIGS. 7A-H showed the dynamic course of anti-tumor effects which lasted 74 min; in the figures, I denotes colon cancer cell, II denotes sensitized cell, III denotes small lymphocyte, IV denotes viscous substance, V denotes pipeline.

Example 8

The Course that Cell Populations with Anti-Tumor Immune Response Activity Kill Tumor Cells Co-culturing breast cancer cell lines (ATCC HTB-22) and peripheral blood mononuclear cells obtained from healthy donors in the three-dimensional culture unit (1) constructed by the method "1". The methods of culture are the same as the former method.

FIGS. 8A-H (40×) showed that the course in which two breast cancer cells were killed and phagocytized by a number of sensitized cells at $10^{th}$ day of culture can be described as follows: firstly, sensitized cells perforated on the tumor cells, then the cytoplasm of tumor cells flowed out along the perforation; in succession, other sensitized immune cells contacted with the breast cancer cells to attack them, (for example, it peeled off part cell membrane of the tumor cells) and at last, the tumor cells were phagocytized by sensitized or activated macrophages. FIGS. 8A-H showed the course that cell populations with anti-tumor immune response activity killed tumor cells, which lasted 130 min. In the figures, I denotes breast cancer cells, II denotes sensitized cells, III denotes macrophages.

Example 9

The Course that Cell Populations with Anti-Tumor Immune Response Activity Dissolve a Liver Cancer Cell Co-culturing liver cancer cell lines SMMC 7721 and peripheral blood mononuclear cells obtained from healthy donors in the three-dimensional culture unit (1) constructed by the method "1", then observing the interrelationship between sensitized cells and liver cancer cell. The methods of culture are same with former method.

FIGS. 9A-H (40×) showed the course in which several sensitized cells with anti-tumor immune response activity lysis a liver cancer cell at $4^{th}$ day of culture. It can be observed that the liver cancer cell was dissolved within several minutes when it contacted with sensitized cells. FIGS. 9A-H showed the dynamic course that cell populations with anti-tumor immune response activity lysis a liver cancer cell, which lasted 10 min. In the figures, I denotes liver cancer cells, II denotes sensitized cells.

Replacing SMMC 7721 with ATCC-HB 8065 cell line and culturing it with peripheral blood mononuclear cells according to same method mentioned above. After 10 days of culture, the concentration of AFP in the culture medium of processed specimen reduces to 51.72 ng/ml, but it is 1000 ng/ml in the control specimen (the culture medium of liver cancer cell lines ATCC-HB 8065 without peripheral blood mononuclear cells; other culture conditions and culture time are the same as former method). Conventional immunoassay was used to determine the concentration of AFP.

Example 10

The Tumor-Killing Effect of Macrophage in the Malignant Pleural Effusion

Obtaining tumor cells and mononuclear cells from the malignant pleural effusion of patient who suffered from lung cancer by means of the method, then mixing it with autologous peripheral blood mononuclear cells 3 ml; putting the mixture into the empty cavities of three-dimensional culture unit (1) constructed by the method "1" and culturing it in the culture medium.

FIGS. 10A-H (40×) showed the course that macrophages kill tumor cells: firstly, macrophages have contact with tumor cells, 3 hours and 2 minutes later (presumably by triggering immune response, which started to activate immune cells), the tumor cells were killed finally by the macrophages. FIGS. 10A-H showed the dynamic course that macrophages kill tumor cells. In the figures, I denotes tumor cell, II denotes macrophage.

Example 11

The Tumor-Killing Effect of Cell Populations with Anti-Tumor Immune Response Activity Obtaining tumor cells and mononuclear cells from the malignant pleural effusion of patient who suffered from lung cancer by means of the method, then mixing it with autologous peripheral blood mononuclear cells 3 ml; putting the mixture into the empty cavities of three-dimensional culture unit (1) constructed by the method "1" and culturing it in the culture medium.

The results showed the course in which the tumor cells in the malignant pleural effusion were attacked by the sensitized cell populations with anti-tumor immune response activity; the tumor size was reduced obviously and finally disappeared; see FIG. 11 (40). FIGS. 11A-H showed the dynamic course of the tumor-killing effect of cell populations with anti-tumor immune response activity, which lasted 3 days. In the figures, I denotes tumor cells, II denotes cell populations with anti-tumor immune response activity.

Example 12

The Biological Effects of Sensitized Cells Activated by Colon Cancer Cell when it Contacts with Colon Cancer Cell Again Adding colon cancer cell lines Lovo and peripheral blood mononuclear cells obtained from healthy persons into the three-dimensional culture unit (1) constructed by the method "1"; then culturing it in the culture medium; the composition of the culture medium is same as the former method; at $14^{th}$ day of cell culture, making use of the method to separate mononuclear cells with anti-tumor immune response activity from the culture, one then observes the biological effects of sensitized cells activated by colon cancer cell when it has contact with the colon cancer cell again in the three-dimensional culture unit.

From FIG. 12, we can see that two mature sensitized cells got together and formed a combined unit of sensitized cells (FIG. 12A, 40×); a close contact between the colon cancer cells and the mononuclear cells can be established within 2 hours of culture in the three-dimensional culture device (FIG. 12B, 40×); 10 days after cell culture, the sensitized cells with anti-tumor effect adhered and covered on the surfaces or at the edges of tumor cells so as to prevent the growth and the transfer of tumor cells (FIG. 12C, 40×); moreover, it can also form capsule at the edges of tumor, which led to malignant tumors showing the morphological characteristics similar to that of benign tumor (FIG. 12D, 40×); 20 days later, a large number of colon cancer cells Lovo died (FIGS. 12E-F, 20×). In the figures, I denotes tumor cells, II denotes sensitized cells, III denotes capsule.

At the same time, the concentration of carcinoembryonic antigen in the culture medium of processed specimen was 11.33 ng/ml, but it was 65.43 ng/ml in the control specimen (the culture medium of colon cancer cell lines Lovo without peripheral blood mononuclear cells; other culture conditions and culture time are the same as the former method). Conventional immunoassay was used to determine the concentration of carcinoembryonic antigens.

Example 13

The Culture of Sensitized Cell Populations with Anti-Tumor Immune Response Activity in the Two-Dimensional Culture System Separating sensitized cell populations with anti-tumor immune response activity cultured in the three-dimensional culture system from tumor cells and culturing them in the two-dimensional culture system, then observe the growth of cells which is showed in the FIGS. 13A-B (A, 20×; B, 40×).

From FIG. 13, we can see that a large number of immune cells can be found in the two-dimensional culture system; in addition, there were no tumor cells in the culture system. These immune cells can be collected and amplified further to appropriate concentration to meet the needs of clinical application.

Example 14

The Preparation of Dendritic Cell

Obtaining tumor cells and mononuclear cells from the malignant pleural effusion of patient who suffered from lung cancer by means of the method, then mixing it with autologous peripheral blood mononuclear cells 3 ml; putting the mixture into the empty cavities of three-dimensional culture unit (2) constructed by the method "1" and culturing it in the culture medium.

From FIGS. 14A-H, we can see that the morphological characteristics of dendritic cell were similar to mature DC after 21 days of culture. Moreover, it had a good motility. In the figures, III denotes dendritic cells. These cells can be collected and amplified further to appropriate concentration so as to meet the needs of clinical treatment.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be within the scope of the invention defined by the appended claims of the application.

The invention claimed is:

1. A method for preparing cell populations with anti-tumor immune response activity, wherein the method includes:
   (1) co-culturing tumor cells and mononuclear cells for 7-28 days in a three-dimensional cell culture device, thereby obtaining a culture which comprises cell populations with anti-tumor immune response activity;
   (2) separating the cell population with anti-tumor immune response activity from the culture which is obtained by step (1);
   wherein, the three-dimensional cell culture device includes:
   (a) a container with liquid cell culture medium; and
   (b) a three-dimensional cell culture unit in the liquid cell culture medium, the three-dimensional cell culture unit is formed of biodegradable material which melts at a temperature of about 50° C. to about 100° C. and are solid at a temperature of 25° C. to about 37° C.; comprises one or more empty cavities used for cell culture, wherein the empty cavity walls define the empty-cavities;
   the empty cavity walls are comprised of a biodegradable material to which cells can adhere and grow and the cavity walls are permeable to the nutritional substances and the products of cell metabolism;
   wherein the biodegradable material of the cavity walls of the three dimensional culture device is nonopaque and is at least one selected from the group consisting of agar, agarose, hydrogels, collagen, and matrigel; and
   wherein the tumor cells and mononuclear cells are put together in the one or more empty cavities of the three-dimensional cell culture unit within the cell culture medium thereby forming a co-culture of tumor cells and mononuclear cells resulting in a cell population with anti-tumor immune response activity.

2. The method of claim 1, wherein the cell population with anti-tumor immune response activity comprises one or more of: tumor-infiltrating lymphocytes, lymphokine-activated killer cells, natural killer cells, tumor-associated macrophages, activated killer monocytes, cytotoxic T lymphocytes and/or dendritic cells.

3. The method of claim 1, wherein the co-culture of tumor cells and mononuclear cells has a ratio of mononuclear cells to tumor cells which is in the range of 5:1 to 100:1.

4. The method of claim 1, further comprising adding a substance that can promote the growth of mononuclear cells into the liquid cell culture medium in the three-dimensional cell culture device in step (1), wherein the substance is a cytokine.

5. The method of claim 1, wherein antigen-presenting cells are added into the liquid cell culture medium in the three-dimensional cell culture device co-culture of step (1).

6. A cell population with anti-tumor immune response activity, prepared by the method of claim 1 wherein the number of cells in the population is from $10^5$ to $10^{11}$.

7. A kit, wherein the kit includes:
   a container,
   and a cell population with anti-tumor immune response activity in the container, prepared by the method of claim 1, wherein the number of cells in the population is from $10^5$ to $10^{11}$.

8. A method for the treatment of a patient having a tumor, wherein the method includes the step of injecting an infusion solution that contains the cell population with anti-tumor immune response activity prepared by the method of claim 1 into a cancer patient in need of the treatment, wherein the mononuclear cells are derived from the patient.

9. A pharmaceutical composition for active specific immunotherapy for administration to a patient in need of the treatment, comprising using the cell population with anti-tumor immune response activity obtained by the method of claim 1, wherein the mononuclear cells in the co-culture are derived from the patient.

* * * * *